(12) United States Patent
Koczab

(10) Patent No.: US 6,204,210 B1
(45) Date of Patent: *Mar. 20, 2001

(54) COMPOSITE NONWOVEN MATERIAL FABRICATION, PROCESS AND APPLICATION TO ABSORBENT HYGIENIC ARTICLES

(75) Inventor: Jean-Pierre Koczab, Bondues (FR)

(73) Assignee: Avgol, Ltd., Holon (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,156

(22) PCT Filed: Sep. 6, 1996

(86) PCT No.: PCT/FR96/01366

§ 371 Date: Jun. 8, 1998

§ 102(e) Date: Jun. 8, 1998

(87) PCT Pub. No.: WO97/09952

PCT Pub. Date: Mar. 20, 1997

(30) Foreign Application Priority Data

Sep. 15, 1995 (FR) .................................. 95 11067

(51) Int. Cl.[7] ...................................... B32B 5/06
(52) U.S. Cl. ................. 442/388; 442/389; 156/73.1; 428/198; 604/378; 604/379
(58) Field of Search .................................. 442/388, 389; 428/198, 138, 219, 137; 604/378, 379, 380; 156/73.1

(56) References Cited

U.S. PATENT DOCUMENTS

| | | | |
|---|---|---|---|
| 5,257,982 | * | 11/1993 | Cohen et al. ................. 604/378 |
| 5,556,392 | * | 9/1996 | Koczab ......................... 604/378 |
| 5,704,101 | * | 1/1998 | Majors et al. ................. 26/18.6 |
| 5,851,204 | * | 12/1998 | Mizutani ....................... 604/385.2 |

FOREIGN PATENT DOCUMENTS

| | | |
|---|---|---|
| 0 072 948 A1 | 3/1983 | (EP) . |
| 0 241 041 A2 | 10/1987 | (EP) . |
| 241041 | * 10/1987 | (EP) ............... A61F/5/44 |
| 0 358 031 A2 | 3/1990 | (EP) . |
| 2 588 285 | 4/1987 | (FR) . |
| 2 698 385 | 5/1994 | (FR) . |
| 2 055 690 | 3/1981 | (GB) . |
| 2 272 917 | 6/1994 | (GB) . |
| WO 87/07117 | 12/1987 | (WO) . |
| WO 88/05269 | 7/1988 | (WO) . |

* cited by examiner

Primary Examiner—William Krynski
Assistant Examiner—J. M. Gray
(74) Attorney, Agent, or Firm—Burns, Doane, Swecker & Mathis, L.L.P.

(57) ABSTRACT

A composite nonwoven material having two external layers, formed of body fluid permeable nonwoven material, between which is arranged a synthetic fiber lap which is permeable to body fluids. The external layers are assembled between each other by thermal fusion according to a pattern forming a network of points and a central area of perforations. The composite nonwoven material can be used to make absorbent hygienic articles.

13 Claims, 2 Drawing Sheets

Figure 1:
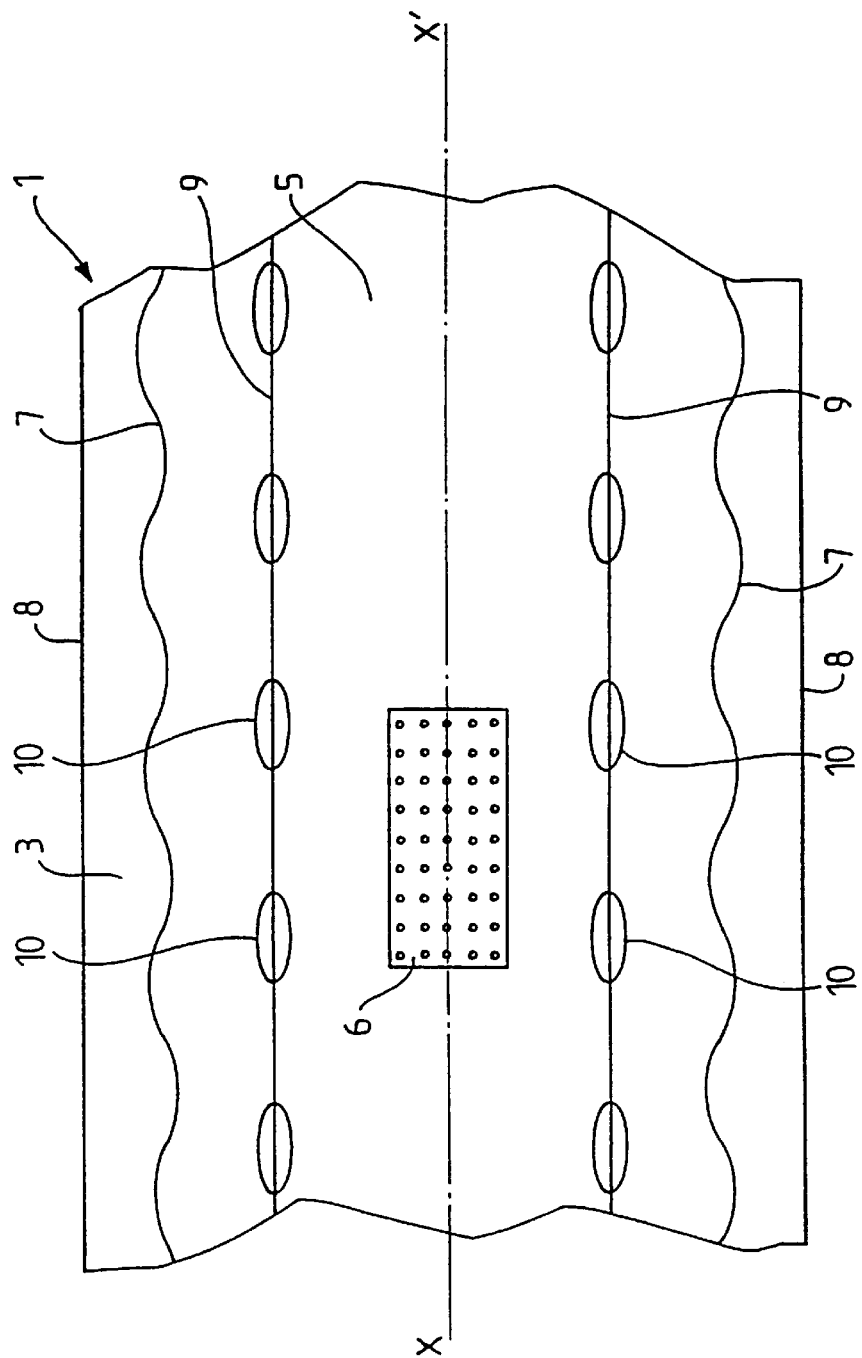

COMPOSITE NONWOVEN MATERIAL FABRICATION, PROCESS AND APPLICATION TO ABSORBENT HYGIENIC ARTICLES

The present invention relates to a composite nonwoven material which, when used as a surface web or, in addition to the surface web, as a band in the crotch zone, above the absorbent pad in an absorbent hygienic article, such as diaper pants or an incontinence lining, makes it possible to improve the rate at which the urine passes through this nonwoven material in the direction of the absorbent pad, whilst limiting the backflow of urine towards the user's skin (rewetting), thus ensuring that the skin is better isolated from the absorbent pad of the hygienic article.

In general terms, absorbent hygienic articles, such as diaper pants and incontinence linings, comprise an outer layer or sheet made of material impermeable to body fluids, such as urine, and an inner layer or surface web permeable to body fluids, a pad or cushion of absorbent material being arranged between said layers.

The purpose of this surface web permeable to body fluids is to isolate the skin from the moistened absorbent pad. Consequently, the surface web must have a suitable degree of softness and must ensure that the urine passes through quickly in the direction of the absorbent pad, whilst forming an obstacle to the return of the urine towards the user's skin.

The document FR-A-2,588,285 describes a multilayer nonwoven textile having at least two nonwoven web layers, one of the layers being formed from fibers of bilobed cross section and the other layer being formed from fibers of trilobed cross section.

Each web layer is preferably obtained by means of the spunbonded technique and the two web layers are joined to form the multilayer nonwoven by thermal bonding in compacted and discontinuous zones.

The document WO 87/07117 describes an absorbent hygienic article comprising an absorbent body surrounded by a sheath. This sheath or surface web consists of two layers of nonwoven material. The first layer of nonwoven material, in contact with the user's skin, consists of a thin layer of spunbonded fibrous cloth and of a hydrophobic material, and the second layer, in contact with the absorbent body, is a hydrophobic fibrous layer of meltbonded fibrous cloth having a design similar to that of the first layer. These two surface web layers are not bonded to one another in the zone intended to come into contact with the user's body.

The document WO 88/05269 relates to a surface web for a disposable absorbent article, composed of at least two nonwoven layers which may be identical or different and which are joined by means of lines of adhesive forming an open pattern.

The document FR-A-2,698,385 describes a composite nonwoven material comprising at least one layer composed of a nonwoven permeable to body fluids and, on this first layer, a fiber lap of the carded type, permeable to body fluids, the fiber lap of the carded type being bonded to the first layer by needling. This composite nonwoven material can be used as a surface web in an absorbent hygienic article. An object of the present invention is, therefore, to provide a composite nonwoven material having a desired degree of softness as well as an improved rate of passage of liquids and improved rewetting resistance, as compared with the prior nonwovens described above and used hitherto to form the surface webs of absorbent hygienic articles. Another object of the present invention is to provide an absorbent hygienic article, such as diaper pants and incontinence linings, comprising preferably a surface web formed from such a composite nonwoven material, the cost of manufacturing said article being reduced due to the characteristics of said composite nonwoven material. Yet another object of the present invention is to provide a method for manufacturing such a composite nonwoven material. According to the present invention, a composite nonwoven material is produced, comprising two outer layers of a nonwoven permeable to body fluids, a synthetic fiber lap permeable to body fluids being arranged between said layers, characterized in that at least the outer layers are assembled together by hot melting according to a pattern forming a network of spots, and in that they comprise, furthermore, a perforated central zone. Advantageously, the two outer nonwoven layers consist of natural or synthetic textile fibers selected from cellulose, viscose, polyester, polyethylene, polypropylene, nylon or ethylene/propylene copolymer fibers.

Also advantageously, the intermediate lap is of the carded type or of the type with nonbonded continuous filaments, said lap consisting of synthetic textile fibers of polyester, polyethylene, polypropylene, nylon or ethylene/propylene copolymers.

The outer layers and the intermediate lap may advantageously have respectively a weight per unit area of between 5 and 15 m/m$^2$ for the layers and between 5 and 30 g/m$^2$ for the lap. Moreover, the upper outer nonwoven layer comprises a hydrophilic longitudinal central zone delimited by continuous weld lines made between at least the two outer layers and forming barriers to the transverse diffusion of body fluids.

Another subject of the present invention is an absorbent hygienic article, such as diaper pants, which comprises an outer layer impermeable to body fluids, an absorbent pad permeable to body fluids, which is secured to this outer layer, and a surface web permeable to body fluids, covering the absorbent pad and secured to the outer layer, the surface web consisting of the abovedescribed composite material according to the invention, the upper outer nonwoven layer provided with a hydrophilic central zone forming the layer intended to be first in contact with the body fluids and therefore the body of the user.

The invention also relates to an absorbent hygienic article comprising an outer layer impermeable to body fluids, an absorbent pad permeable to body fluids and secured to the outer layer, and comprising two widened opposite end parts and a narrower crotch zone, a crotch zone band permeable to body fluids, of a width similar to the crotch zone of the pad and of a length similar to the pad, and a surface web permeable to body fluids and secured to the outer layer, the crotch zone band consisting of the composite nonwoven material according to the invention, the upper outer nonwoven layer provided with a hydrophilic central zone being oriented so as to be in contact with the body fluids first or immediately after the surface web.

Advantageously, the crotch zone band is arranged between the absorbent pad and the surface web.

The invention also provides a method for manufacturing a composite nonwoven material, which comprises the steps involving:

unwinding simultaneously a synthetic fiber lap permeable to body fluids and two nonwoven laps permeable to body fluids, inserting the synthetic fiber lap between the two nonwoven laps, feeding the assembly as a whole to a calendering device, allowing uniform spot bonding between at least the nonwoven laps by hot melting, feeding the composite band obtained through a perforation device in order to obtain a perforated central zone.

Advantageously, the method comprises the step involving feeding the composite band to a welding device, making it possible to produce, on the one hand, a first pair of continuous weld lines symmetrical to the longitudinal center axis of the band, between at least the two nonwoven laps, in the vicinity of each longitudinal edge of said band, and, on the other hand, a second pair of continuous weld lines which are also symmetrical to the longitudinal center axis of the band and the transverse spacing of which is smaller than that of the first pair and which thus delimits a hydrophilic longitudinal central zone on the upper face of said composite nonwoven material.

Advantageously, the calendering, perforation and welding devices may be of the ultrasonic type.

Figure 2:
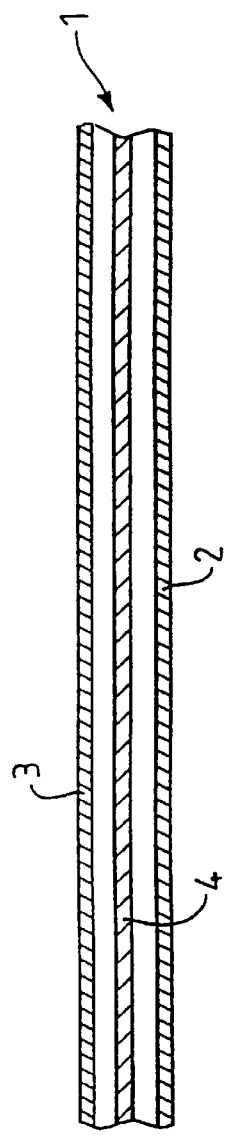
Figure 3:
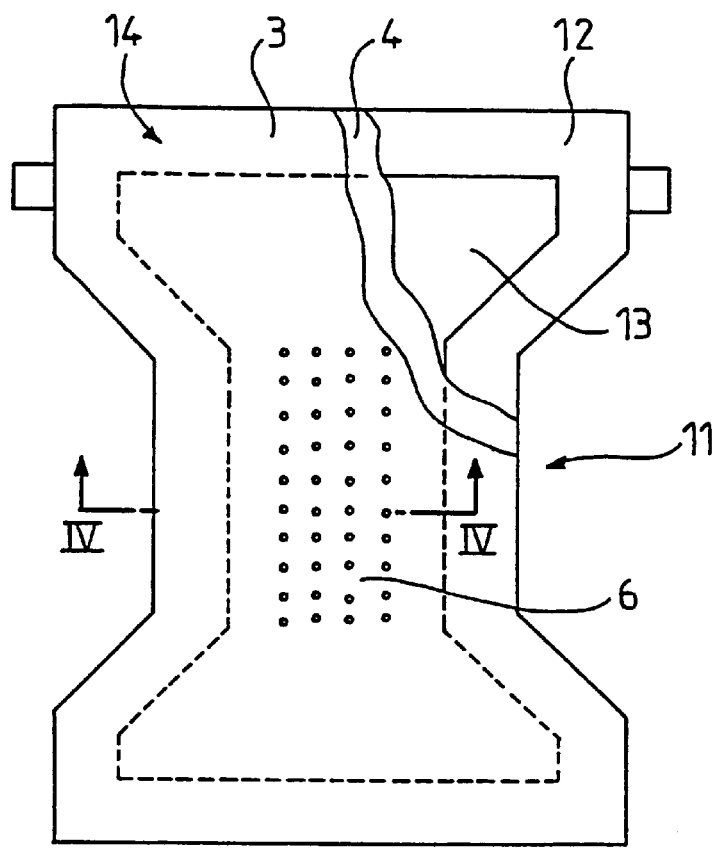
Figure 4:
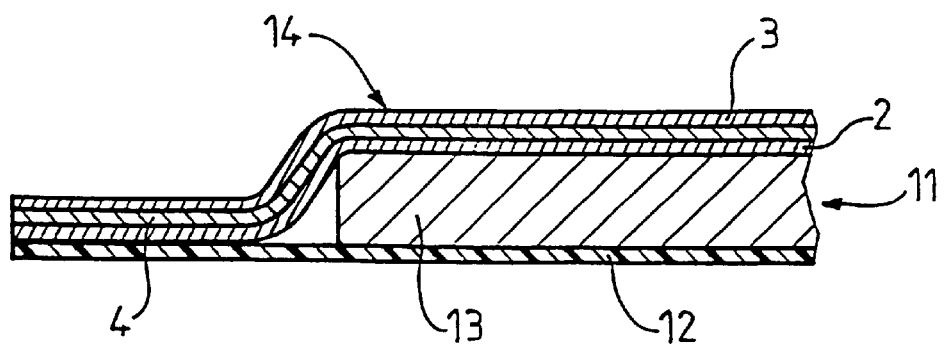

Furthermore, the perforated central zone may be continuous or discontinuous and have a width smaller than that of the hydrophilic central zone of the upper outer nonwoven layer. The rest of the description refers to the accompanying figures of which:

FIG. 1 shows a partial top view of the composite nonwoven material according to the invention, FIG. 2 shows a diagrammatic sectional view of the composite nonwoven material according to the invention, before the calendering and welding steps, FIG. 3 shows a partially cut away top view of an absorbent hygienic article, such as diaper pants, comprising a surface web consisting of the composite material according to the invention, and FIG. 4 shows a sectional view taken along the line IV—IV of FIG. 3.

Referring to FIGS. 1 and 2, these show the composite nonwoven material 1 according to the invention.

This material comprises a first and second outer layer 2, 3 made of nonwoven permeable to body fluids, such as urine, a synthetic fiber lap 4 permeable to body fluids being inserted between said layers, the assembly as a whole being fixed together by the hot melting of at least the outer layers.

All types of conventional nonwovens, consisting, for example, of natural or synthetic textile fibers, such as cellulose, viscose, polyester, polyethylene, polypropylene, nylon or ethylene/propylene copolymer fibers, may be used for the outer nonwoven layers 2, 3. These outer nonwoven layers may consist of a nonwoven manufactured by all conventional methods, such as, for example, spunbonding, thermal bonding, chemical bonding, bonding by air blowing, spunlacing. Preferably, these layers have a weight per unit area of between 5 and 15 g/m². The upper outer layer 3 comprises a hydrophilic central zone 5, whilst the lower outer layer 2 may be hydrophilic or hydrophobic.

The synthetic fiber lap 4 permeable to fluids is of the carded type or consists of nonbonded continuous filaments and may consist of synthetic textile fibers, such as polyester, polyethylene, polypropylene, nylon or ethylene/propylene copolymers. Polyester fibers are particularly recommended for their characteristics of resilience and good fluid transport. In general, the lap 4 has a weight per unit area of between 5 and 30 g/m² and the denier of the fibers of this lap is generally between 3 and 13.

We shall describe the method for manufacturing such a composite material according to the invention.

The cohesion of the composite nonwoven material 1 is obtained by subjecting the assembly consisting of the layers 2, 3 and of the lap 4, after they have been superposed and brought into contact, to a hot calendering operation, so as to fix together at least the outer layers 2, 3 by hot melting according to a pattern forming a network of spots.

It is clear that, depending on the nature of the fibers selected for the layers 2 and 3, if the intermediate lap 4 consists of polyester fibers, there will be no melting of the fibers of the layers 2 and 3 with the polyester fibers, in view of the considerable differences in the melting temperatures of these polymers. This applies to the preferred embodiment, where the layers 2 and 3 consist of polypropylene fibers and have a weight per unit area of 10 g/m², the polyester fiber lap 4 likewise having a weight per unit area of 10 g/m². However, the use of fibers having melting points which are identical or which are sufficiently close to one another to ensure fusion between the layers and the lap is conceivable.

The calendering device used is of the ultrasonic type (with a sonotrode and an anvil), the rotary anvil of which carries relief patterns intended for forming the hot melting spots which may, as a practical example, be of cylindrical shape, of a diameter of 1 mm and arranged so as to form a meshwork of staggered spots with a distance between two successive spots in a row of 7 mm.

However, other types of meshwork are possible. The advantage of such a calendering device is its flexibility of use.

Furthermore, devices other than ultrasonic devices may be used, such as heated calendering rolls.

The next step in the manufacturing method is the operation of perforating the composite material; this is carried out by passing the latter through a second ultrasonic device of higher power.

The shape of the wheels of the anvil which are used for this operation is a function of the desired dimension of the perforations.

In a suitable exemplary embodiment, the perforations have a diameter of 1 to 2 mm and the distance between two successive perforations is 10 mm.

As shown in FIG. 1, the perforation zone 6 is centered on the center longitudinal axis XX' of the composite material and is located within the hydrophilic central zone 5 of the outer layer 3. This perforation zone may, for example, have a width of 40 mm and a length of 100 mm, when it is discontinuous, as in FIG. 1. In this case, the interval of this zone 6 must correspond to the production interval for a pair of diaper pants, so that it is possible, on the production line, to incorporate this material as the surface web of diaper pants and center the perforation zone in the crotch zone of the diaper pants, said zone receiving the urine.

Finally, the last steps in the manufacture of the composite material are the operations of welding by also passing it through ultrasonic devices.

They comprise a first welding assembly which makes it possible to produce two first continuous longitudinal weld lines 7, at least between the outer layers 2 and 3, which are symmetrical to the axis XX' and are arranged in the vicinity of the longitudinal edges 8 of the composite band 1. Preferably, these weld lines 7 may be of sinusoidal shape and at a distance from the longitudinal edges 8 of approximately 5 mm. They thus form barriers to the transverse migration of the body fluids absorbed by the composite material 1 which is used as a surface web of diaper pants.

A second welding assembly makes it possible to produce two second continuous longitudinal weld lines 9, at least between the outer layers 2 and 3, which are likewise symmetrical to the center axis XX'. The distance between these two lines 9 may, for example, be 90 mm for a composite material 1 having a breadth of 330 mm; these weld lines 9 delimit the hydrophilic central zone 5 of the composite material 1 and have the main function of forming a first barrier watertight against the transverse diffusion of body fluids, such as urine, when said composite material 1 is used as a surface web in diaper pants.

The second welding assembly may also be designed, in addition, to form continuous lines of decorative discontinuous weld patterns 10 which may assume shapes as diverse as those of flowers or birds or various geometric shapes (ovals, circles, etc.).

Referring to FIGS. 3 and 4, these show an absorbent hygienic article 11, such as diaper pants, comprising an outer layer 12 made of a flexible material impermeable to body fluids, such as urine, and an absorbent pad 13 permeable to body fluids and having a dimension smaller than that of the outer layer being secured to said layer. The absorbent pad 13 is secured to the impermeable layer 12 by any conventional means, such as by adhesive bonding. Arranged on this absorbent pad 13 is a surface web 14 permeable to body fluids and having a dimension similar to that of the outer layer 12. The surface web 14 is bonded, on the periphery of the absorbent pad 13, to the outer layer 12 by any means, such as by adhesive bonding. As is well known in the art, the outer layer 12, the absorbent pad 13 and the surface web 14 have the shape of an hourglass comprising two relatively wide opposite end parts joined by means of a narrower crotch part or zone. As shown in FIGS. 3 and 4, the surface web consists of the composite nonwoven material 1 shown in FIGS. 1 and 2, which comprises two outer nonwoven layers 2 and 3 and an intermediate synthetic fiber lap 4. As the figures show, the upper outer layer 3, provided with a hydrophilic central zone 9 and with a perforation zone 6, forms the innermost layer of the web, said layer being intended to come into contact with the body of the user of the hygienic article 11.

A hygienic article according to the invention is thus produced which has improved properties of softness, of rate of passage of body fluids and of a barrier to rewetting. When it is used in addition to a conventional surface web, the composite material according to the invention is preferably used in the form of a crotch zone band having a width similar to that of the crotch zone of the absorbent pad and a length similar to that of this pad. In this embodiment, which is not illustrated in the figures of the present patent application, the crotch zone band consisting of the composite material according to the invention is preferably arranged between the conventional surface web and the absorbent pad, in such a way that the upper outer nonwoven layer 3 comes into direct contact with the surface web.

The invention thus provides a composite nonwoven material which is particularly useful and economical in the manufacture of surface webs for absorbent hygienic articles.

What is claimed is:

1. A composite nonwoven material comprising:
   a lower outer layer made of a nonwoven material permeable to body fluids and having a first melting point,
   an upper outer layer made of a nonwoven material permeable to body fluids and having a melting point near said first melting point,
   a synthetic fiber lap permeable to body fluids being arranged between said outer layers, said fiber lap comprising loose carded filaments made of a material having a second melting point substantially higher that said first melting point, the outer layers being assembled together by hot melting according to a pattern forming a network of spots, said hot melting having been made at a temperature near said first melting point so that the filaments of said fiber lap remain unmelted when said upper and lower outer layers are hot melted,
   the upper outer nonwoven layer comprising a hydrophilic longitudinal central zone delimited by continuous weld lines made between the two outer layers and forming barriers to the transverse diffusion of body fluids, and
   said hydrophilic longitudinal central zone including a perforated central zone having perforations extending all the way through the outer layers and the synthetic fiber lap.

2. Composite nonwoven material according to claim 1, wherein the outer nonwoven layers consist of natural or synthetic textile fibers selected from cellulose, viscose, polyester, polyethylene, polypropylene, nylon or ethylene/propylene copolymer fibers.

3. Composite nonwoven material according to claim 1, wherein the intermediate synthetic fiber lap is of the carded type or of the type with nonbonded continuous filaments.

4. Composite nonwoven material according to claim 1, wherein the intermediate synthetic fiber lap consists of synthetic textile fibers selected from polyester, polyethylene, polypropylene, nylon or ethylene/propylene copolymer fibers.

5. Composite nonwoven material according to claim 1, wherein the outer nonwoven layers have a weight per unit area of between 5 and 15 $g/m^2$.

6. Composite nonwoven material according to claim 1, wherein the intermediate synthetic fiber lap has a weight per unit area of between 5 and 30 $g/m^2$.

7. The composite woven material of claim 1, wherein the first temperature equals the second temperature.

8. An absorbent hygienic article comprising:
   an outer layer impermeable to body fluids,
   an absorbent pad permeable to body fluids and secured to the outer layer, and
   a surface web permeable to body fluids, covering the absorbent pad and secured to the outer layer,
   wherein the surface web comprises the composite nonwoven material according to claim 1, the upper outer nonwoven layer provided with the hydrophilic central zone forming the layer intended to be first in contact with the body fluids and therefore the body of the user.

9. An absorbent hygienic article comprising:
   an outer layer impermeable to body fluids,
   an absorbent pad permeable to body fluids and secured to the outer layer, and comprising two widened opposite end parts joined by a narrower crotch zone,
   a crotch zone band permeable to body fluids and of a width similar to the crotch zone of the pad and of a length similar to the pad, and
   a surface web permeable to body fluids and secured to the outer impermeable layer, on the periphery of the absorbent pad, wherein the crotch zone band comprises the composite nonwoven material according to claim 1, the upper outer nonwoven layer provided with the hydrophilic central zone being oriented so as to be in contact with the body fluids first or immediately after the surface web.

10. Absorbent hygienic article according to claim 9, wherein the crotch zone band is arranged between the absorbent pad and the surface web.

11. A method for manufacturing a composite nonwoven material, comprising the steps of:

unwinding simultaneously a synthetic fiber lap permeable to body fluids and two nonwoven laps permeable to body fluids, inserting the synthetic fiber lap between the two nonwoven laps, feeding the assembly as a whole to a calendering device, allowing uniform spot bonding between at least the nonwoven laps by hot melting to obtain a composite band, and feeding the assembly to a performation device in order to obtain a perforated central zone, through the composite band, subsequently feeding the composite band to a welding device to produce a first pair of continuous weld lines, symmetrical to a longitudinal center axis of the band, between at least the two nonwoven laps, in the vicinity of each longitudinal edge of said band, and, to produce a second pair of continuous weld lines which are symmetrical to the longitudinal center axis of the band, and the transverse spacing of which is smaller than that of the first pair and which thus delimits a hydrophilic longitudinal central zone on the upper face of said composite nonwoven material, said hydrophilic longitudinal central zone including the perforated central zone.

12. The method according to claim 11, wherein the calendering, perforation and welding devices are of the ultrasonic type.

13. The method according to claim 11, wherein the perforated central zone may be continuous or discontinuous and has a width smaller than that of the hydrophilic central zone of the upper outer nonwoven lap.

* * * * *